(12) United States Patent
Bernstein

(10) Patent No.: US 7,285,544 B2
(45) Date of Patent: Oct. 23, 2007

(54) USE OF NITROXIDES IN TREATING SKIN DISEASE

(76) Inventor: Eric F. Bernstein, 221 Righters Mill Rd., Gladwyne, PA (US) 19035

( * ) Notice: Subject to any disclaimer, the term of this patent is extended or adjusted under 35 U.S.C. 154(b) by 0 days.

(21) Appl. No.: 10/991,822

(22) Filed: Nov. 18, 2004

(65) Prior Publication Data

US 2005/0124593 A1    Jun. 9, 2005

Related U.S. Application Data

(60) Provisional application No. 60/523,016, filed on Nov. 18, 2003.

(51) Int. Cl.
*A61K 31/56* (2006.01)
*A61K 31/445* (2006.01)
*A61K 33/40* (2006.01)

(52) U.S. Cl. .................. 514/171; 514/256; 514/315; 424/616

(58) Field of Classification Search .............. None
See application file for complete search history.

(56) References Cited

U.S. PATENT DOCUMENTS

| | | | |
|---|---|---|---|
| 4,857,533 A * | 8/1989 | Sherman et al. | 514/282 |
| 5,462,946 A | 10/1995 | Mitchell et al. | 514/315 |
| 5,679,374 A * | 10/1997 | Fanchon et al. | 424/450 |
| 5,728,714 A * | 3/1998 | Proctor | 514/315 |
| 5,817,632 A | 10/1998 | Hsia | 514/21 |
| 5,824,781 A | 10/1998 | Hsia | 530/385 |
| 5,840,701 A | 11/1998 | Hsia | 514/21 |
| 5,840,734 A | 11/1998 | Bernstein | 514/315 |
| 6,552,040 B1 | 4/2003 | Bernstein | 514/315 |
| 6,576,259 B2 * | 6/2003 | Yamashita et al. | 424/468 |
| 2003/0007939 A1 * | 1/2003 | Murad | 424/61 |

OTHER PUBLICATIONS

Stedman's Medical Dictionary, 25th Edition, published 1990 by Williams & Wilkins, (MD), pp. 15, 16, 93, 494, 533, 1508.*
The Merck Index, 11th Edition, published 1989 by Merck & Co., Inc. (NJ), p. 757, citation #4710.*
Goffman et al., "Topical Application of Nitroxide Protects Radiation-Induced Alopecia in Guinea Pigs", Int. J. Radiation Oncology Biol. Phys. 1992 22:803-806.
Mitchell et al.,"Inhibition of Oxygen-Dependent Radiation-Induced Damage by the Nitroxide Superoxide Dismutase Mimic, Tempol", Archives of Biochemistry and Biophysics 1991 289:62-70.
Mitchell et al., "Biologically Active Metal-Independent Superoxide Dismutase Mimics", Biochemistry 1990 29:2802-2807.
Nilsson et al., "Inhibition of Lipid Peroxidation by Spin Labels", J. Biol. Chem. 1989 264 (19):11131-11135.
Samuni et al., "Superoxide Reaction with Nitroxide Spin-Adducts", Free Radical Biology & Medicine 1989 6:141-148.
Samuni et al., "A Novel Metal-free Low Molecular Weight Superoxide Dismutase Mimic", J. Biol. Chem. 1988 263 (34):17921-17924.

\* cited by examiner

*Primary Examiner*—Raymond J Henley, III
(74) *Attorney, Agent, or Firm*—Licata & Tyrrell P.C.

(57) ABSTRACT

Methods of treating inflammatory skin diseases such as rosacea, atopic dermatitis, contact dermatitis, drug eruptions, psoriasis, seborrheic dermatitis, connective tissue diseases, autoimmune disorders, urticaria or hives, and inflammation associated with skin infections by topical or systemic administration of a nitroxide containing compound are provided.

5 Claims, No Drawings

USE OF NITROXIDES IN TREATING SKIN DISEASE

This patent application claims the benefit of priority from U.S. Provisional Patent Application Ser. No. 60/523,016, filed Nov. 18, 2003, which is herein incorporated by reference in its entirety.

BACKGROUND OF THE INVENTION

Inflammation is a significant component in a number of skin disorders or diseases including, but not limited to, acne and rosacea, atopic dermatitis, contact dermatitis, drug eruptions, psoriasis, seborrheic dermatitis, connective tissue diseases (such as lupus, scleroderma, and rheumatoid arthritis), other autoimmune disorders such as the blistering disease bullous pemphigoid or pemphigus, pigmentary diseases (such as post inflammatory hyperpigmentation, melasma and vitiligo), urticaria or hives, inflammation associated with skin infections such as tinea corporis or fungal infection of the finger or toenails, among others.

Modulating the inflammatory response has been shown to result in dramatic improvement in the conditions listed above. Standard treatment involves the use of topical corticosteroids, oral corticosteroids and other agents that modulate inflammation.

However, topical corticosteroids have undesirable side effects such as skin atrophy, telangiectasia, and the possibility of adrenal axis suppression thus limiting their long-term use.

Significant research has been conducted in the field of radiation therapy to assess the ability of free-radical scavengers in protecting normal tissue from ionizing radiation.

Sulfhydryl compounds were among the first radioprotectors to be identified. Their protective mechanism appears to be due to their ability to scavenge radiation-induced free radicals and/or donate reducing equivalents to oxidized molecules.

Hematopoietic cytokines have also been investigated as radioprotectors. They are believed to protect by more quickly restoring hematopoietic function after radiation exposure.

Recently, a new class of radioprotectors, referred to as nitroxides, has been described. As a class, nitroxides are stable free radical components which react with a variety of biologically relevant compounds including other free radicals (Nilsson et al. *J. Biol. Chem.*, 1989, 264:11131-11135). The observation that several nitroxides themselves reacted with free radicals, specifically oxy radicals, led to the investigation of these compounds as radioprotectors (Saminu et al. *Free Radical Biol. Med.*, 1989, 6:141-148).

Tempol [4-hydroxy-2,2,6,6-tetramethyl-piperidinyloxy, free radical] is one such example, a piperindinyl-n-oxyl with the n-oxide sterically stabilized by symmetric pairs of adjacent methyl groups. This compound is commercially available through Aldrich Chemical Co., Milwaukee, Wis. It is most commonly used to spin label biological molecules such as NADP.

Tempol has been demonstrated to function as a superoxide dismutase (SOD) mimic, protecting mammalian cells from superoxide generated from hypoxanthine/xanthine oxidase and from hydrogen peroxide mediated cytotoxicity (Mitchell et al. *Biochem.*, 1990, 29:2802-2807; Samuni et al., *J. Biol. Chem.*, 1988, 263:17921-17924). Tempol has also been demonstrated to provide both in vitro and in vivo protection against ionizing radiation (Mitchell et al. *Arch. Biochem. Biophys.*, 1991, 289:62-70) and to protect against radiation-induced alopecia by speeding the recovery of hair growth within a field of heavily irradiated skin (Goffman et al. *Int. J. Rad. Onc. Biol. Phys.*, 1992, 22:803-806). This protection has been suggested to be linked to direct protection of hair follicle stem cells and development of other nitroxides.

U.S. Pat. No. 5,840,734 describes the use of Tempol in prevention of photoaging, sunburn and skin cancer caused by the UVA and UVB rays of sunlight. Additionally, U.S. Pat. No. 6,552,040 describes using other nitroxides in addition to Tempol for photoprotection, and describes using nitroxides including Tempol to augment wound healing.

Nitroxides are stable free radicals with antioxidant catalytic activities similar to superoxide dismutase. Nitroxides existing in vivo have been shown to interact with other substances to also mimic catalase activities.

Nitroxide containing compounds have been described in the art for numerous uses. For example, U.S. Pat. No. 5,462,946 discloses biologically compatible compositions containing an effective amount of a metal independent nitroxide compound for use in protecting the skin against ionizing radiation, mucositis, the effects of whole body radiation and radiation induced hair loss. The nitroxide containing compositions disclosed therein are applied topically as an ointment, lotion or cream, intravenously or orally by pill or lozenge. This patent also teaches the nitroxide containing compounds to be useful as protectants against increased oxygen exposure so as to avoid pulmonary adult respiratory distress syndrome, oxygen-induced lenticular degeneration and hyaline membrane disease in infants, oxidative stress-induced cataracts, reperfusion injury in treating cardiovascular phenomena such as myocardial infarction and strokes, pancreatitis or intestinal ulceration and organ transplant, cytotoxicity due to excess oxidation in animal or plant cell cultures, cytotoxic effects of chemotherapeutic agents, and mutagenic and carcinogenic agents. Also taught in U.S. Pat. No. 5,462,946 is parenteral, intra-articular or oral administration of a nitroxide containing composition in arthritic conditions, parenteral or oral administration of a nitroxide containing composition as an aging retardant and oral or intravenous administration of a nitroxide containing compound in weight reduction.

U.S. Pat. No. 5,824,781, U.S. Pat. No. 5,840,701 and U.S. Pat. No. 5,817,632 teach compositions and processes to alleviate free radical toxicity based on use of nitroxides in association with physiologically compatible macromolecules. These compositions are suggested to be useful as blood substitutes, radioprotective agents, imaging agents, agents to protect against ischemia and reperfusion injury, particularly cerebral stroke, and in vivo enzyme mimics.

SUMMARY OF THE INVENTION

The present invention provides a new use for nitroxide containing compounds. In the present invention nitroxide containing compounds or combinations of nitroxides with other agents are applied topically or administered systemically to alleviate the symptoms and/or treat inflammatory skin disorders. Examples of inflammatory skin diseases or disorders which can be treated or symptoms of which can be alleviated in accordance with the present invention include, but are in no way limited to, rosacea, atopic dermatitis, contact dermatitis, drug eruptions, psoriasis, seborrheic dermatitis, connective tissue diseases such as lupus, scleroderma, and rheumatoid arthritis, other autoimmune disorders such as the blistering disease bullous pemphigoid, pemphigus, pigmentary diseases such as post inflammatory hyperpigmentation, melasma and vitiligo, urticaria or hives, and inflammation associated with skin infections such as tinea corporis or fungal infection of the finger or toenails, among others.

DETAILED DESCRIPTION OF THE INVENTION

Numerous skin diseases or disorders result from inflammation with the associated release of mediators from a variety of inflammatory and resident cells. Neutrophils, mast cells and lymphocytes orchestrate an inflammatory response that results in significant release of inflammatory mediators, and the creation of numerous free radicals. Skin diseases in which inflammation is a significant component include, but are not limited to acne and rosacea, atopic dermatitis, contact dermatitis, drug eruptions, psoriasis, seborrheic dermatitis, connective tissue diseases (such as lupus, scleroderma, and rheumatoid arthritis), other autoimmune disorders such as the blistering disease bullous pemphigoid or pemphigus, pigmentary diseases (such as post inflammatory hyperpigmentation, melasma and vitiligo), urticaria or hives, inflammation associated with skin infections such as tinea corporis or fungal infection of the finger or toenails, among others. Inflammation is the key step to most of these diseases, and the production of free radicals enhances or maintains the inflammatory response in many cases. In addition, free radicals cause the majority of damage and maintain changes in skin architecture to a large degree.

It is now believed that topical application or systemic administrations of a composition comprising a nitroxide containing compound is useful in treating and/or alleviating the symptoms of inflammatory skin diseases. By systemic administration it is meant to include, but is not limited to, oral, intravenous, or sublingual administration or intra-muscular or subcutaneous injection.

For purposes of the present invention, by "nitroxides" or "nitroxide containing compound" it is meant stable nitroxide free radicals. Examples of nitroxide containing compounds are well known in the art and taught in prior art references such as U.S. Pat. No. 5,462,946, the teachings of which are herein incorporated by reference in their entirety.

Examples of inflammatory skin diseases which can be treated and/or the symptoms alleviated include, but are not limited to, rosacea, atopic dermatitis, contact dermatitis, drug eruptions, psoriasis, seborrheic dermatitis, connective tissue diseases such as lupus, scleroderma, and rheumatoid arthritis, other autoimmune disorders such as the blistering disease bullous pemphigoid and pemphigus, pigmentary diseases such as post inflammatory hyperpigmentation, melasma and vitiligo, urticaria or hives, and inflammation associated with skin infections such as tinea corporis or fungal infection of the finger or toenails, among others.

In the present invention, a nitroxide containing compound or a combination of nitroxides with a second agent is applied topically or administered systemically to a subject to alleviate the symptoms and/or treat the inflammatory skin disorder or disease.

By subject it is meant to include any mammal, and in particular humans.

Examples of topically applied compositions comprising a nitroxide containing compound for use in the present invention include, but are not limited to creams, lotions gel, sprays and solutions. Methods of formulating nitroxide containing compounds into creams, lotions, gels, sprays, or solutions, as well as pharmaceutical additives for such formulations, are well known to those skilled in the art. The topically applied nitroxide containing formulations may further comprise a second agent useful in treatment of the inflammatory skin disorder such as a topical antibiotic or topical corticosteroids in the same preparation.

Methods for preparation of formulations for systemic administration of a nitroxide containing compound are also well known.

Examples of second agents which can be co-administered in the same formulation or at the same time as the nitroxide containing compound include, but are not limited to, alpha-hydroxy acids, poly-hydroxy acids, antibiotics, benzoyl peroxide, hydroquinone, kojic acid, corticosteroids, and tacrolimus.

What is claimed:

1. A method for treating or alleviating symptoms of an inflammatory skin disease or disorder consisting of administering to a subject suffering from an inflammatory skin disease or disorder a nitroxide containing compound wherein the inflammatory skin disease is rosacea, atopic dermatitis, contact dermatitis, a drug eruption, psoriasis, seborrheic dermatitis, urticaria or hives, so that the inflammatory skin disease or disorder is treated or its symptoms alleviated.

2. The method of claim 1 wherein the nitroxide containing compound is applied topically to the skin of the subject in a cream, lotion, gel, spray or solution.

3. A method for treating or alleviating symptoms of an inflammatory skin disease or disorder comprising administering to a subject suffering from an inflammatory skin disease or disorder a nitroxide containing compound wherein the inflammatory skin disease is rosacea, atopic dermatitis, contact dermatitis, a drug eruption, psoriasis, seborrheic dermatitis, urticaria or hives, or inflammation associated with a skin infection wherein the nitroxide containing compound is administered orally, intravenously, by sublingual administration, or by intra-muscular or subcutaneous injection.

4. A method for treating or alleviating symptoms of an inflammatory skin disease or disorder consisting of administering to a subject suffering from an inflammatory skin disease or disorder a nitroxide containing compound and a second agent comprising an alpha-hydroxy acid, a poly-hydroxy acid, an antibiotic, benzoyl peroxide, hydroquinone, kojic acid, a corticosteroid or tacrolimus, wherein the inflammatory skin disease is rosacea, atopic dermatitis, contact dermatitis, a drug eruption, psoriasis, seborrheic dermatitis, urticaria or hives, so that the inflammatory skin disease or disorder is treated or its symptoms alleviated.

5. The method of claim 4 wherein the nitroxide containing compound is applied topically to the skin of the subject in a cream, lotion, gel, spray or solution.

* * * * *